(12) United States Patent
Orkin

(10) Patent No.: US 8,038,055 B2
(45) Date of Patent: Oct. 18, 2011

(54) BLOOD AND MEDICAL SPECIMEN COLLECTION

(76) Inventor: Fredric I. Orkin, Highland Park, IL (US)

(*) Notice: Subject to any disclaimer, the term of this patent is extended or adjusted under 35 U.S.C. 154(b) by 0 days.

(21) Appl. No.: 12/510,546

(22) Filed: Jul. 28, 2009

(65) Prior Publication Data

US 2010/0044429 A1    Feb. 25, 2010

Related U.S. Application Data

(60) Provisional application No. 61/089,989, filed on Aug. 19, 2008.

(51) Int. Cl.
| | | |
|---|---|---|
| G06F 17/00 | (2006.01) | |
| G06F 19/00 | (2011.01) | |
| G06Q 30/00 | (2006.01) | |
| G06Q 90/00 | (2006.01) | |
| G06Q 50/00 | (2006.01) | |

(52) U.S. Cl. ........ 235/375; 235/385; 700/214; 700/215; 705/2; 705/3; 600/300

(58) Field of Classification Search ............... 235/375, 235/385; 700/214, 215; 705/2–3
See application file for complete search history.

(56) References Cited

U.S. PATENT DOCUMENTS

| | | |
|---|---|---|
| 3,831,006 A | 8/1974 | Chaffin, III et al. |
| 4,835,372 A | 5/1989 | Gombrich et al. |
| 5,164,575 A | 11/1992 | Neeley et al. |
| 5,781,442 A | 7/1998 | Engleson et al. |
| 6,599,481 B2 | 7/2003 | Stevens et al. |
| 2004/0039607 A1* | 2/2004 | Savitz et al. ............. 705/3 |
| 2004/0267562 A1* | 12/2004 | Fuhrer et al. ............ 705/2 |
| 2005/0110640 A1* | 5/2005 | Chung ............... 340/572.1 |
| 2006/0138211 A1* | 6/2006 | Lubow ................ 235/375 |
| 2007/0290028 A1* | 12/2007 | Fox et al. ............. 235/375 |
| 2008/0217391 A1* | 9/2008 | Roof et al. ............ 235/375 |

* cited by examiner

*Primary Examiner* — Michael G Lee
*Assistant Examiner* — Laura Gudorf
(74) *Attorney, Agent, or Firm* — The Webb Law Firm

(57) ABSTRACT

In a method of tracking a specimen acquired from a patient, machine-readable codes present on a patient identification (ID), an order to obtain a specimen from the patient, and on a specimen-taker ID means, respectively, are stored in a computer storage. A specimen container having a fourth machine-readable code preapplied thereto is selected from a plurality of specimen containers having unique machine-readable codes preapplied thereto. In response to a processor determining that the first and second machine-readable codes are related to the same patient, the processor causes the first—fourth machine-readable codes to be relationally stored in the computer storage. Responsive to the processor receiving a signal that a specimen has been placed in the selected specimen container, the processor causes an indication thereof to be stored in the computer storage in a relational manner with the first—fourth machine-readable codes.

19 Claims, 4 Drawing Sheets

SPECIMEN TYPES

STANDARD BLOOD (INCLUDING TYPE AND CROSS MATCH)

BLOOD CULTURES

URINE CULTURES

STOOL CULTURES

VAGINAL SWABS

RECTAL SWABS

SPINAL FLUID

RAPE KIT

WOUND CULTURES

SKIN SCRAPINGS

JOINT ASPIRATIONS

ORAL SWABS

AMNIOTIC FLUID

TISSUE BIOPSIES

FIG. 2

BLOOD AND MEDICAL SPECIMEN COLLECTION

CROSS REFERENCE TO RELATED APPLICATION

This application claims priority to U.S. Provisional Patent Application No. 61/089,989, filed Aug. 19, 2008, which is incorporated herein by reference.

BACKGROUND OF THE INVENTION

1. Field of the Invention

The present invention relates to the collection of blood and medical specimens, for example, in a medical facility, such as a hospital.

2. Description of Related Art

In today's hospitals, mislabeling of specimen tubes, vials, or collection containers is a common problem that poses grave medical risk to a patient and potentially high liability to the institution. Despite best efforts at training and automation of the process with computers and barcodes, errors persist. The number of specimens collected and blood draws is quite high for a typical hospital. Error rates at or close to zero have been an unachievable goal.

Mislabeling errors can include: wrong patient name; missing label; mis-communicated order; outdated tube, vial, or container; unreadable, smudged, or bruised label; tube, vial, or container not labeled at bedside in accordance with applicable standards; and contamination while handling tube, vial, or container to add label. For the purpose of simplicity, hereinafter, the word "vial" will be utilized to describe the prior art in the present invention, and it is to be understood that "vial" means any specimen collection vessel deemed suitable and/or desirable by one skilled in the art for the collection of a specimen from a patient. Accordingly, "vial" is to be understood as being, without limitation, a vial, a tube, or a container.

Staff that attach labels to specimen vials in most modern hospitals can include: a floor nurse; a phlebotomist; a patient care technician; an emergency room nurse; an operating room nurse; a surgical floor nurse; and a lab technician.

The core problem has been identified to involve: failure to verify patient identity typically at the bedside; failure to use two forms of patient identity independent of a medical record number; and failure to verify that the patient identity matches the patient information on the printed label to be attached to the specimen vial.

Most hospitals use a wrist (or ankle) identification (ID) band to identify each patient with information that at minimum includes the patient's name and date of birth. Modern hospitals either use or are considering using a barcode to encode this and possibly other patient information on the ID band at registration to automate the capture of the patient's information without human error.

Although barcodes on ID bands work well after registration, some emergency room (ER) trauma patients are moved immediately to a bed where a specimen is drawn in anticipation of a medical doctor (MD) order and prior to full registration where the barcoded ID band is produced. These patients may use a handwritten ID band or an ID band without a barcode. Mistakes in getting the correct label onto the proper specimen vial are well documented. Unused full blood vials drawn in anticipation of an MD order are also at high risk of being labeled for the wrong patient as patients are moved with some frequency in the ER.

In the rest of the hospital, i.e., other than the ER, a typical, prior art flow diagram for collecting a specimen is shown in FIG. 1. The many types of specimens that are routinely collected are shown in FIG. 2.

With reference to FIG. 1, a method of collecting a specimen (e.g., a blood specimen) in accordance with the prior art includes step 2, where a suitable medical professional, e.g., a medical doctor (MD), a physician's assistant, etc., places an order to draw the blood specimen from a patient who is desirably already wearing a conventional ID band that includes at least the patient's name and date of birth, but which may not include any computer-readable code, such as, without limitation, a patient barcode.

After the order is placed in step 2, the method advances to step 4 where the order to draw the blood specimen from the patient is entered into a computer in any suitable and/or desirable manner, e.g., without limitation, by a data entry person. Thereafter, the method advances to step 6 where barcode labels associated with the order are printed. These printed barcode labels may include one or more of the following: one or more order barcode labels, one or more patient barcode labels, and/or one or more vial barcode labels to be applied to one or more specimen vials that either will receive or have already received a specimen.

Thereafter, in step 8, the barcode labels printed in step 4 are retrieved, perhaps from a printer that has also printed other, unrelated barcode labels. In step 10, these retrieved barcode labels and the patient are brought together (e.g., in the patient's room) where, in step 12, the specimen-taker determines whether the patient is wearing an ID band. If not, the method advances to step 14 where appropriate corrective action is taken to prepare an ID band for the patient and fasten it to the patient.

From either step 12 or step 14, the method advances to step 16 where the specimen-taker manually compares information on the patient's ID band to like information on the printed barcode labels. This information desirably includes, among other things, a medical record number, the patient's name, and the patient's date of birth. If, in step 18, the specimen-taker determines that the information on the patient's ID band does not match like information on the printed barcode labels, the method advances to step 20 where appropriate corrective action is taken to make the information on the patient's ID band and the like information on the printed barcode labels match.

From either step 18 or step 20, the method advances to step 22 where the specimen-taker collects the specimen (in this example a blood specimen) in one or more specimen vials. In step 24, the specimen-taker applies at least one of printed vial barcode labels to each specimen containing vial. In practice, the order of steps 22 and 24 may be reversed. Once each specimen vial contains a specimen and has one of the printed vial barcode labels applied thereto, the specimen vial is sent to the lab for analysis of the specimen.

In view of the prior art method of collecting a specimen described above being known to result in mislabeling of specimen vials, it would be desirable to provide a method and system that reduces or avoids such mislabeling of specimen vials.

SUMMARY OF THE INVENTION

Disclosed is a method of tracking a specimen acquired from a patient. The method comprises: (a) storing in a computer storage accessible by a standalone or networked computer a first machine-readable code present on an identification (ID) means worn by a patient; (b) storing in the computer storage a second machine-readable code associated with an order to obtain a specimen from the patient; (c) storing in the computer storage a third machine-readable code present on an identification (ID) means worn by a specimen-taker; (d) following steps (a)-(c), selecting from a plurality of specimen containers having machine-readable codes that are unique to each other preapplied thereto one specimen container including a fourth machine-readable code preapplied thereto; (e) in response to an electronic reading means reading and dispatching to a processor of the computer the first—fourth machine-readable codes present on the ID means worn by the patient, present on the order, present on the ID means worn by the specimen-taker, and present on the specimen container, respectively, and in response to the processor determining that the first machine-readable code and the second machine-readable code are related to the same patient, the processor causing said first—fourth machine-readable codes to be stored in the computer storage in a relational manner and the processor of the computer causing a signal to be generated to acquire a specimen from the patient and to place the acquired specimen in the container; and (f) responsive to the processor receiving a signal that the specimen has been placed in the container following step (e), the processor causing an indication thereof to be stored in the computer storage in a relational manner with said first—fourth machine-readable codes.

The method can further include: (g) in response to the electronic reading means reading and dispatching to the processor of the computer a fifth machine-readable code that is preapplied to another specimen container selected from the plurality of specimen containers, said processor causing the first, second, third, and fifth machine-readable codes to be stored in the computer storage in a relational manner; and (h) responsive to the processor receiving a signal that the other specimen has been placed in the other container following step (g), the processor causing an indication thereof to be stored in the computer storage in a relational manner with said first, second, third, and fifth machine-readable codes.

Each machine-readable code can be unique of the other machine-readable codes.

Step (f) can include the processor determining whether the signal of step (f) is received within a predetermined time interval of the processor generating the signal of step (e) and storing an indication thereof in the computer storage in a relational manner with said first—fourth machine-readable codes.

Each machine-readable code can comprise a unique barcode. The ID means worn by the patient can be a bracelet. The ID means worn by the specimen-taker can be a badge.

The first machine-readable code can comprise a barcode that encodes at least one of the following: a unique serial number; the patient's name; a registration number assigned to the patient; the patient's date of birth; the patient's sex; a code that signifies the type if ID means worn by the patient; and a check digit.

The fourth machine-readable code can comprise a barcode that encodes at least one of the following: a unique serial number; an expiration date; a color of a lid or cap that specifies the type of specimen the container is to be used for; human readable numbers and/or characters corresponding to one or more of the unique serial number, the expiration date, and the color of the lid; and a check digit.

The second machine-readable code can comprise a barcode that encodes at least one of the following: an order number; a type of specimen to be acquired; a volume of the specimen to be acquired; a time that the specimen is to be acquired; and a control number.

The electronic reading means can be an optical scanner that is communicatively coupled with the computer via a wired or wireless connection. The optical scanner can be a barcode scanner.

Also disclosed is a method of tracking a specimen acquired from a patient. The method comprises: (a) storing in a computer storage of a computer a first machine-readable code present on an identification (ID) means worn by a patient; (b) storing in the computer storage of the computer a second machine-readable code associated with an order to obtain a specimen from the patient; (c) storing in the computer storage of the computer a third machine-readable code present on an identification (ID) means worn by a specimen-taker; (d) following steps (a)-(c), selecting from a plurality of specimen containers having machine-readable codes that are unique to each other preapplied thereto one specimen container including a fourth machine-readable code preapplied thereto, wherein the fourth machine-readable code comprises a barcode that encodes a unique serial number and an expiration date of the container; (e) in response to receiving the fourth machine-readable code from an electronic reading means, a processor of the computer determining from the expiration date encoded in the fourth machine-readable code if the specimen container is out-of-date and, if so, causing an alert signal indicative of said out-of-date condition to be generated by or near the electronic reading means, otherwise, if the specimen container is not out-of-date, and in response to the processor determining that the first machine-readable code and the second machine-readable code are related to the same patient, the processor causing the first—fourth machine-readable codes to be stored in the computer storage in a relational manner and the processor causing a signal to be generated to acquire a specimen from the patient and to place the acquired specimen in the container; and (f) responsive to the processor receiving a signal that the specimen has been placed in the container following step (e), the processor causing an indication thereof to be stored in the computer storage in a relational manner with said first—fourth machine-readable codes.

The method can further include: (g) in response to receiving from the electronic reading means a fifth machine-readable code that is preapplied to another specimen container selected from the plurality of specimen containers, said processor causing the first, second, third, and fifth machine-readable codes to be stored in the computer storage in a relational manner; and (h) responsive to the processor receiving a signal that the other specimen has been placed in the other container following step (g), the processor causing an indication thereof to be stored in the computer storage in a relational manner with said first, second, third, and fifth machine-readable codes.

Each machine-readable code can be unique of the other machine-readable codes.

Step (f) can include the processor determining whether the signal of step (f) is received within a predetermined time interval of the processor generating the signal of step (e) and storing an indication thereof in the computer storage in a relational manner with said first—fourth machine-readable codes.

Each machine-readable code can comprise a unique barcode. The ID means worn by the patient can be a bracelet. The ID means worn by the specimen-taker can be a badge.

The first machine-readable code can comprise a barcode that encodes at least one of the following: a unique serial number; the patient's name; a registration number assigned to the patient; the patient's date of birth; the patient's sex; a code that signifies the type if ID means worn by the patient; and a check digit.

The fourth machine-readable code can comprise a barcode that encodes at least one of the following: a unique serial number; an expiration date; a color of a lid or cap that specifies the type of specimen the container is to be used for; human readable numbers and/or characters corresponding to one or more of the unique serial number, the expiration date, and the color of the lid; and a check digit.

The second machine-readable code can comprise a barcode that encodes at least one of the following: an order number; a type of specimen to be acquired; a volume of the specimen to be acquired; a time that the specimen is to be acquired; and a control number.

The electronic reading means can be an optical scanner that is communicatively coupled with the computer via a wired or wireless connection. The optical scanner can be a barcode scanner.

Lastly, disclosed is a system for tracking one or more specimens acquired from a patient, wherein a standalone or networked computer is in operative communication with a computer storage and an electronic reading means that is operative for reading unique machine-readable codes disposed on the following: an identification (ID) means worn by a patient, an order to obtain the one or more specimens from the patient, an identification (ID) means worn by a specimen-taker, and a plurality of specimen containers each for receiving one specimen from the patient.

The electronic reading means is also operative for dispatching said machine-readable codes to the processor which, in response to the machine-readable codes for the patient ID means and the order being related to the same patient, stores the machine-readable code for each specimen container to receive a specimen in the computer storage in a relational manner with the machine-readable codes for the patient ID means, the order, and the specimen-taker ID means, and generates a signal to acquire a specimen from the patient and to place the acquired specimen in the container.

The computer is responsive to a signal that a specimen that has been placed in each specimen container for storing an indication thereof in the computer storage in a relational manner with the machine-readable code for each specimen container that received the specimen stored in the computer storage. Each specimen container of the plurality of specimen containers has a machine-readable code preapplied thereon that is unique from the machine-readable code preapplied to any other of the specimen containers and the machine-readable codes disposed on the patient ID means, the order, and the specimen-taker ID means.

BRIEF DESCRIPTION OF THE DRAWINGS

FIG. 2 is a list of exemplary patient specimens that are routinely collected;

DETAILED DESCRIPTION OF THE INVENTION

Figure 1:
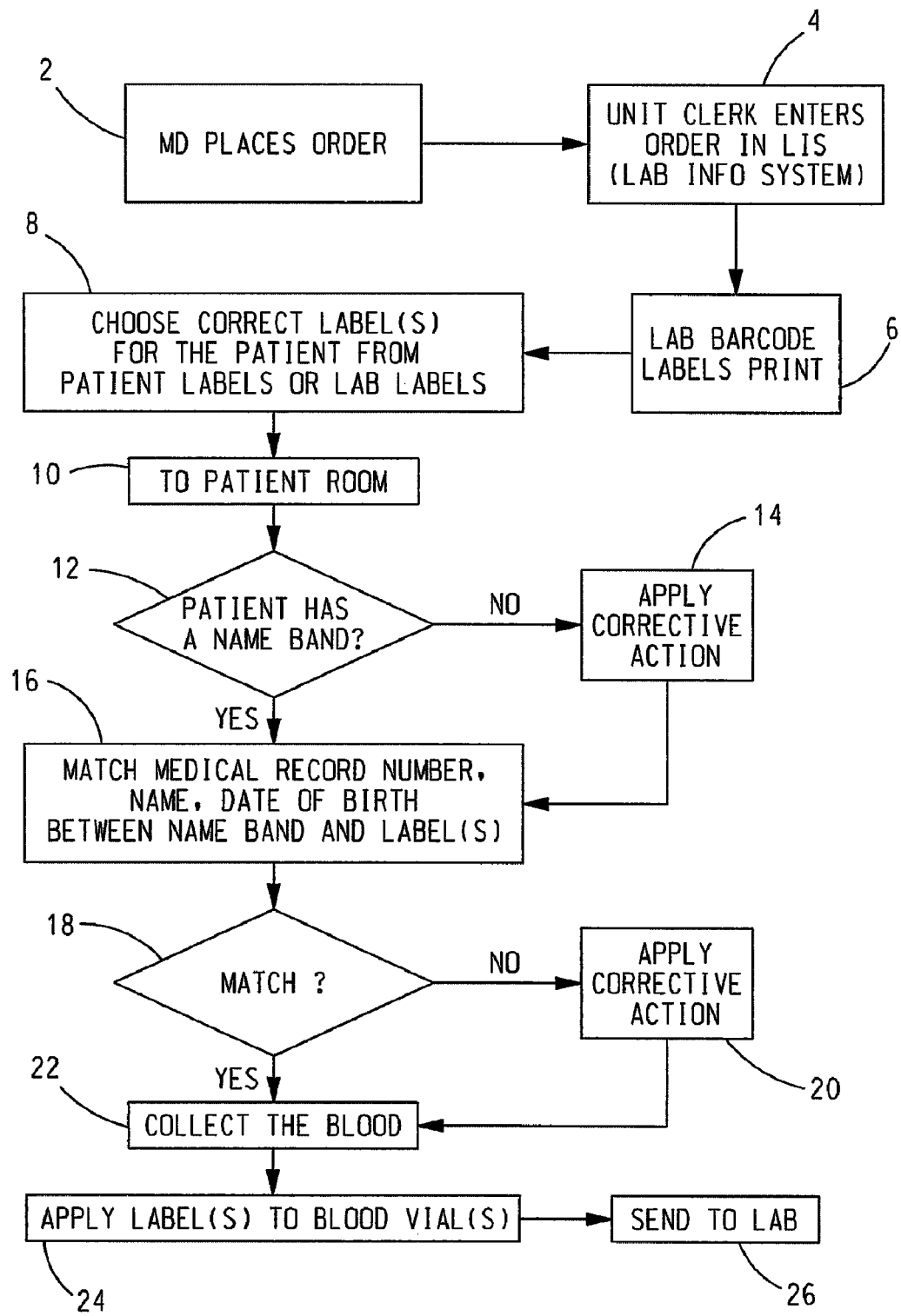
FIG. 1 is a flow diagram of a prior art method for collecting a specimen.
Figure 3:
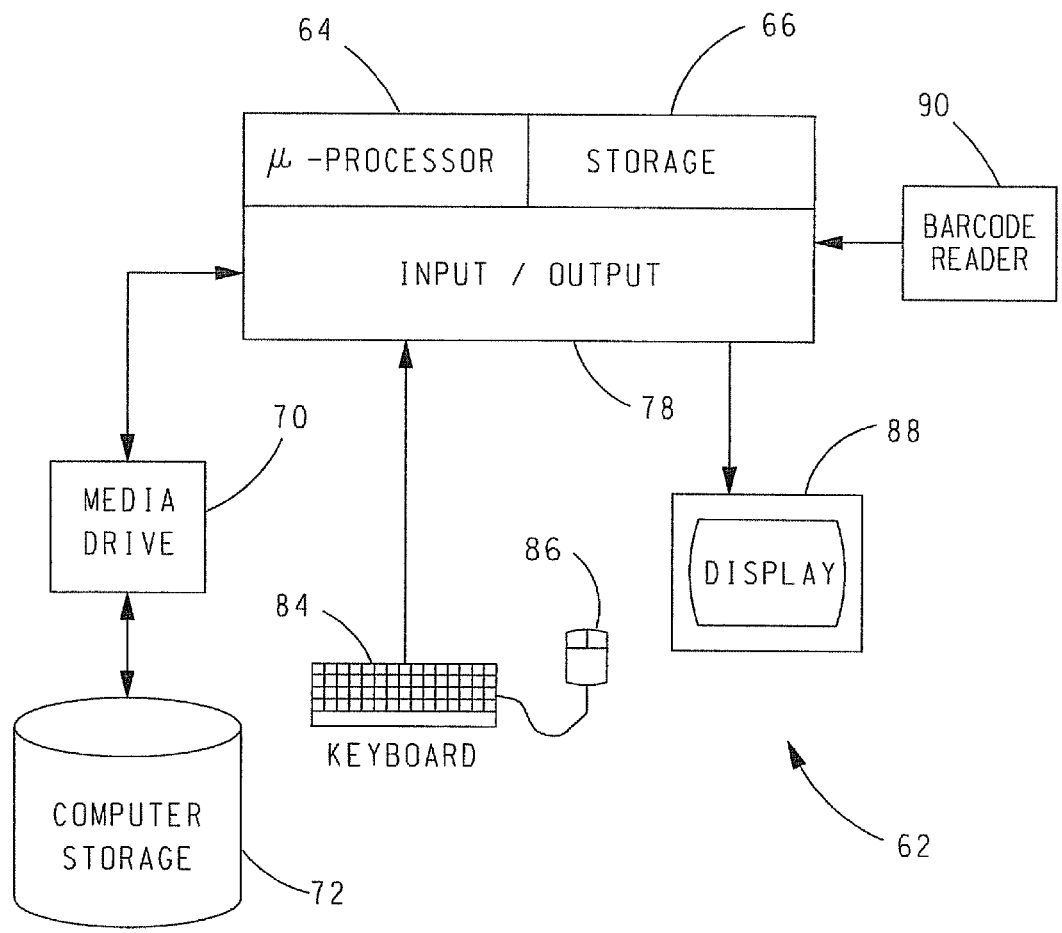
FIG. 3 is a block diagram of an exemplary computer that can be utilized to implement the present invention.

With reference to FIG. 3, the present invention is embodied, at least in part, in a software program which executes on one or more standalone or networked computers 62. Each computer 62 is coupled, either directly or via a wired or wireless computer network, to a local or remote computer storage 66, such as RAM memory, FLASH memory, a Hard Disk Drive, etc., of the type known in the art. Each computer 62 can also include a media drive 70, such as a CD-ROM drive, and the like, which can operate with a portable computer storage 72, e.g., a CD-ROM, capable of storing computer software, data, and the like. Each computer 62 includes at least one microprocessor 64 or other such processing means that enables computer 62 to process and store data in computer storage 66 or computer storage 72 under the control of the software program, which operates under the control of a computer operating system, that controls the operation of computer 62 to process data, store data, and output data in human readable format (via print or visual display) in a manner known in the art. The software program can be stored in computer storage 66, computer storage 72, or some combination of computer storages 66 and 72. The software program is able to configure and operate computer 62 in a manner to implement some or all of the present invention. Each computer 62 can include an input/output system 78 that can include, among other things, a keyboard 84, a mouse 86, and/or a display 88. Computer 62 is exemplary of a computer that is capable of executing the software program of the present invention and is not to be construed as limiting the invention.

Figure 4:
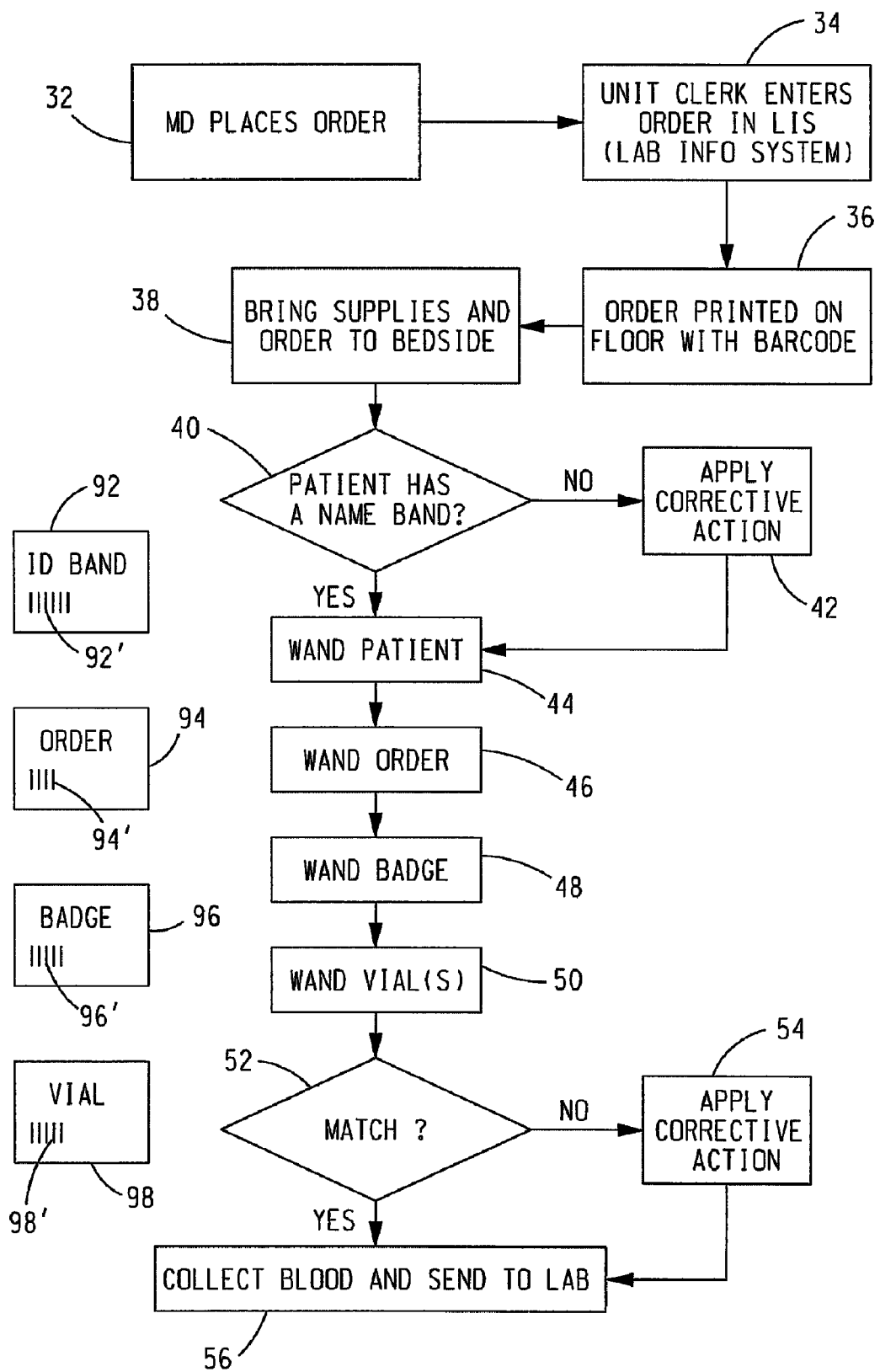
FIG. 4 is a flow diagram of a method for collecting a specimen in accordance with the present invention.

With reference to FIG. 4 and with continuing reference to FIG. 3, a method of collecting a specimen in accordance with the present invention includes a step 32 where a suitable medical professional, e.g., a medical doctor, a physician's assistant, etc., places an order to draw the specimen, e.g., a blood specimen, from a patient who is desirably already wearing an ID band 92 that desirably includes a computer generated patient barcode number 92' that is unique to the patient, i.e., no two patients currently in the medical facility are assigned the same patient barcode number. As used herein, "barcode number" may include an alpha, numeric, or alphanumeric sequence.

At or about the time the computer generates the patient barcode number 92' on ID band 92, the processor of the computer creates in the computer storage a database data structure where the patient's information, e.g., the patient's name and the patient's date of birth, are stored in a relational manner with the patient's barcode number. The patient's information can be entered in any suitable and/or desirable manner, e.g., without limitation, by order entry personnel, at or about the time the patient is accepted into the medical facility.

After the order is placed in step 32, the method advances to step 34 where an order to draw the blood specimen from the patient is entered into the computer in any suitable and/or desirable manner, e.g., without limitation, by data entry personnel such as a lab clerk. At or about the time the order to draw the blood specimen is entered, the processor of the computer generates a unique order barcode number 94' and stores this order barcode number 94' in a relational manner in the database data structure where the patient's information and the patient's barcode number 92' are stored in a relational manner. Desirably, no two orders currently in the medical facility are assigned the same order barcode 94'.

In step 36, the computer, either automatically or under the control of the data entry person, generates a hard copy of the order 94 that includes the unique computer assigned order barcode 94', some or all of the patient's information, and, optionally, the patient's barcode number 92'. The alpha, numeric, or alphanumeric sequence represented by each barcode number described herein may appear in conventional human readable form, i.e., letters, numbers, etc., next to each hardcopy of the barcode number to facilitate manual entry of the barcode number.

At this point in time, the computer storage includes the database data structure where the patient's information, the order barcode number 94', and the patient's barcode number 92' are stored in a relational manner. Because the combination of at least the patient's barcode number 92' and the order barcode number 94' are unique with respect to all other combinations of patient barcode numbers and order barcode numbers present in the medical facility, no other data structure having the same patient barcode number and order barcode number should exist in the computer storage.

In step 38, the printed order 94, including unique order barcode number and, desirably, some or all of the patient's information, along with suitable blood drawing supplies are brought to the patient (e.g., at the patient's bedside) where, in step 40, the blood drawer (or blood-taker) determines whether the patient is wearing an ID band 92 that includes a unique patient barcode number 92'. To determine whether the patient's barcode number 92' is unique, the barcode number on the ID band is input into the computer whereupon the processor compares said input patient barcode number 92' to each other patient barcode number stored in data structures in the computer storage. If the patient is either not wearing an ID band or is wearing an ID band that the processor determines does not have a unique patient barcode number, an ID band having a unique patient barcode number is prepared for the patient and fastened to the patient in step 42. The ID band can include, without limitation, a wrist band, an ankle band, and the like.

Following either step 40 or step 42, the patient barcode 92' on the patient's ID band 92 is input into the computer in step 44. As used herein, "input into the computer" means that a barcode number is either manually input into the computer (e.g., without limitation, via a keyboard, a computer mouse, and/or any other suitable and/or desirable manual input means) or is read by a suitable barcode reading means, e.g., barcode reader 90 in FIG. 3, that communicates the read barcode number to the processor of the computer which is in communication with the barcode reading means and which is operatively coupled to the computer storage. Each barcode number represents a machine-readable code that can be read by the suitable reading means, in this case barcode reading means 90.

In steps 46, 48, and 50 the order barcode number 94' on the order 94 is input into the computer, a badge barcode number 96' present on a badge 96 of the blood drawer is input into the computer, and one or more barcode number(s) 98' preapplied to specimen vial(s) 98 where the drawn blood is to be stored is/are input into the computer, respectively. Each barcode number input into the computer is stored at least temporarily by the processor in the computer storage. The order of input of barcode numbers into the computer in steps 44, 46, 48 and 50 is not to be construed as limiting the invention. Each barcode number (albeit, patient barcode number 92', order barcode number 94', blood drawer barcode number 96', and vial barcode number 98') is unique and, more specifically, each vial has a unique vial barcode number 98' preapplied thereto.

In step 52, the processor determines if a database data structure exists that includes the patient's barcode number 92' input into the computer in step 44 and order barcode number 94' input into the computer in step 46. In other words, the processor determines if the patient's barcode number 92' and the order barcode number 94' are related to the same patient. If so, the processor causes the barcode number 96' on the badge 96 of the blood drawer input into the computer in step 48 and each barcode number 98' preapplied to a vial 98 that was input into the computer in step 50 to be stored in a relational manner in the database data structure with the patient's barcode number 92' and the order barcode number 94'. Desirably, the barcode number 96' on the badge 96 of the blood drawer input into the computer in step 48 and each vial barcode number 98' preapplied to a vial 98 that was input into the computer in step 50 are stored in the same database data structure where the patient's barcode number 92' and the order barcode number 94' were previously stored in a relational manner. However, this is not to be construed as limiting the invention since it is envisioned that each vial barcode number 98' can be stored in a separate database data structure in a relational manner with the patient barcode number 92', the order barcode number 94', and the blood drawer barcode number 96' if desired. Thus, each database data structure can store one vial barcode number 98' or more than one vial barcode number 98' in a relational manner with the corresponding patient barcode number 92', order barcode number 94', and blood drawer barcode number 96'.

On the other hand, should the processor determine that the patient's barcode number 92' and the order barcode number 94' are not related to the same patient in the data structure where these barcodes were previously stored, the method advances from step 52 to step 54 where any discrepancy in the relationship between the patient's barcode number 92' and the order barcode number 94' in the data structure is corrected.

At this point in time, the computer storage includes the database data structure where the patient's information, the order barcode number 94', the patient's barcode number 92', the blood drawer's barcode number 96', and each vial barcode number 98' are stored in a relational manner.

Following either step 52 or 54, the method advances to step 56 where the processor causes one or more suitable signals (audio, visual, or both) to be output that informs the blood drawer to draw the blood sample and send it to a lab for analysis. At or about the time the signal is output in step 56, the processor starts a software or hardware timer that is utilized to determine that the blood draw is completed within a predetermined time after the signal is output in step 56. When collection of the blood specimen in one specimen vial 98 or two or more specimen vials 98 is complete, the blood drawer causes an indication thereof to be input into the computer where the processor stores this indication in a relational manner with the patient's information, the order barcode number 94', the patient's barcode number 92', the blood drawer's barcode number 96', and each vial barcode number 98'.

The processor compares the time between when the signal is output in step 56 and the time when the blood drawer causes the indication that the collection of the blood specimen is complete to be input into the computer (i.e., the specimen collection time) to the predetermined time. The specimen collection time is desirably stored in a relational manner in the same database data structure where the patient's information, the order barcode number 94', the patient's barcode number 92', the blood drawer's barcode number 96', and each vial barcode number 98' are stored in a relational manner. Thus, upon completion of the blood draw, a complete record of the blood drawing event resides in a relational manner in the database data structure stored in the computer storage. If the specimen collection time exceeds the predetermined time, the processor can optionally cause a suitable signal to be output that informs the blood drawer of this fact.

The lab receiving each vial 98 containing a blood sample has all of the order and "label" information stored in the database data structure that is linked to the vial barcode number 98' preprinted on each vial and can process the order with confidence without producing any further paperwork or labels.

Prior to executing the method shown in FIG. 4, at least the patient barcode number 92', the order barcode number 94', and the blood drawer barcode number 96' are stored in the computer storage. As discussed above, the relationship between the patient barcode number 92', the order barcode number 94', the blood drawer barcode number 96', and each vial barcode number 98' can be stored in the database data structure that is stored in the computer storage. For example, in step 52 of the method shown in FIG. 4, in response to barcode reader 90 reading and dispatching to a processor of the computer the patient barcode number 92', the order barcode number 94', the blood drawer barcode number 96', and the barcode number 98' of each vial utilized to collect a sample, and in response to the processor determining that the patient barcode number 92' and the order barcode number 94' are related to the same patient, the processor stores the patient barcode number 92', the order barcode number 94', the blood drawer barcode number 96', and each specimen vial barcode number 98' to be stored in a relational manner in a database data structure that exists in the computer storage. The storage of these barcode numbers in a relational manner in a database data structure stored on the computer storage occurs only after it has been established that the patient barcode number 92' and the order barcode number 94' are related to the same patient. In the method described above, the relationship of the patient barcode number 92' and the order barcode number 94' to the same patient was made by way of these barcodes being stored in a relational manner in the database data structure stored in the computer storage. Thereafter, when the blood drawer barcode number 96' and each specimen vial barcode number 98 is input into the computer, these latter barcode numbers 96' and 98' are stored in a relational manner in the same database data structure as the patient barcode number 92' and the order barcode number 94'. However, this is not to be construed as limiting the invention since the determination that the patient barcode number 92' and the order barcode number 94' are related to the same patient can be made outside of the database data structure whereupon the database data structure is created that relates to various barcode numbers 92', 94', 96', and 98' in a relational manner at the time these barcode numbers are input into the computer in steps 44-50.

Desirably, the barcode number 96' of the blood drawer (or specimen-taker) is stored in the computer storage prior to performing the steps of the method shown in FIG. 4 for security purposes and/or quality control purposes. Thus, if a specimen-taker is not qualified or is not authorized to acquire a particular specimen from a patient, the processor can cause a suitable error signal to be generated when the specimen-taker's badge barcode number 96' is input in step 48.

As noted above, each barcode comprises a unique machine-readable code. The ID band worn by each patient can be in the form of a wrist or ankle bracelet. The badge of the blood drawer (or blood-taker) comprises an ID means that is worn by the blood drawer.

The patient barcode number 92' is desirably a machine-readable code that encodes one or more of the following: a unique serial number; the patient's name; a registration number assigned to the patient; the patient's date of birth; the patient's sex; a code that signifies the type of ID means worn by the patient (ankle or wrist bracelet); and a check digit.

Each vial barcode number 98' is desirably a machine-readable code that encodes one or more of the following: a unique serial number; an expiration date; a color of a lid or cap that specifies the type of specimen the container is to be used for; human readable numbers and/or characters corresponding to one or more digits of the unique serial number, the expiration date, and a check digit.

The order barcode number 94' is desirably a machine-readable code that encodes one or more of the following: an order number; a type of specimen to be acquired; a volume of the specimen to be acquired; a time when the specimen is to be acquired; and a control number.

The barcode reading means 90 comprises an electronic reading means in the form of an optical barcode scanner that is communicatively coupled with the processor of the computer via a wired or wireless connection.

As can be seen, the present invention provides a means of achieving a failsafe, zero defect process for identifying and processing patient specimen samples. It has the additional benefit of eliminating the cost of vial labels (since the vials have preprinted vial barcodes already attached thereto), associated printers, and staff labor in dealing with the vial labels.

The invention has been described with reference to the preferred embodiment. Obvious modifications and alterations will occur to those of ordinary skill in the art upon reading and understanding the preceding detailed description. For example, the specimen collection system described above can be implemented in any suitable and/or desirable manner utilizing one or more standalone or networked computers and local or remote computer storage, all connected by a wired network, a wireless network, or some combination of a wired and wireless network. Moreover, while the invention has been described with reference to the drawing of a blood specimen, this is not to be construed as limiting the invention since it is envisioned that the invention can be utilized in connection with the acquisition of any type of biological specimen, such as, without limitation, each specimen type shown in FIG. 2. It is intended that the invention be construed as including all such modifications and alterations insofar as they come within the scope of the appended claims or the equivalents thereof.

The invention claimed is:

1. A method of tracking a specimen acquired from a patient, the method comprising:
   (a) storing in a computer storage accessible by a standalone or networked computer a first machine-readable code present on an identification (ID) means worn by a patient;
   (b) storing in the computer storage a second machine-readable code associated with an order to obtain a specimen from the patient;
   (c) storing in the computer storage a third machine-readable code present on an identification (ID) means worn by a specimen-taker;
   (d) selecting from a plurality of specimen containers having machine-readable codes that are unique to each other preapplied thereto one specimen container including a fourth machine-readable code preapplied thereto;
   (e) in response to an electronic reading means reading and dispatching to a processor of the computer the first—fourth machine-readable codes present on the ID means worn by the patient, present on the order, present on the ID means worn by the specimen-taker, and present on the specimen container, respectively, and in response to the processor determining that the first machine-readable code and the second machine-readable code are related to the same patient, the processor causing said first—fourth machine-readable codes to be stored in the computer storage in a relational manner and the processor of the computer causing a signal to be generated to acquire a specimen from the patient and to place the acquired specimen in the container; and
   (f) responsive to the processor receiving a signal that the specimen has been placed in the container following step (e), the processor causing an indication thereof to be stored in the computer storage in a relational manner with said first—fourth machine-readable codes, wherein step (f) includes the processor determining whether the signal of step (f) is received within a predetermined time interval of the processor generating the signal of step (e) and storing an indication thereof in the computer storage in a relational manner with said first—fourth machine-readable codes.

2. The method of claim 1, further including:

(g) in response to the electronic reading means reading and dispatching to the processor of the computer a fifth machine-readable code that is preapplied to another specimen container selected from the plurality of specimen containers, said processor causing the first, second, third, and fifth machine-readable codes to be stored in the computer storage in a relational manner; and (h) responsive to the processor receiving a signal that the other specimen has been placed in the other container following step (g), the processor causing an indication thereof to be stored in the computer storage in a relational manner with said first, second, third, and fifth machine-readable codes.

3. The method of claim 2, wherein each machine-readable code is unique of the other machine-readable codes.

4. The method of claim 1, wherein:

each machine-readable code comprises a unique barcode;
the ID means worn by the patient is a bracelet; and
the ID means worn by the specimen-taker is a badge.

5. The method of claim 1, wherein the first machine-readable code comprises a barcode that encodes at least one of the following: a unique serial number; the patient's name; a registration number assigned to the patient; the patient's date of birth; the patient's sex; a code that signifies the type of ID means worn by the patient; and a check digit.

6. The method of claim 1, wherein the fourth machine-readable code comprises a barcode that encodes at least one of the following: a unique serial number; an expiration date; a color of a lid or cap that specifies the type of specimen the container is to be used for; human readable numbers and/or characters corresponding to one or more of the unique serial number, the expiration date, and the color of the lid; and a check digit.

7. The method of claim 1, wherein the second machine-readable code comprises a barcode that encodes at least one of the following: an order number; a type of specimen to be acquired; a volume of the specimen to be acquired; a time that the specimen is to be acquired; and a control number.

8. The method of claim 1, wherein the electronic reading means is an optical scanner that is communicatively coupled with the computer via a wired or wireless connection.

9. The method of claim 8, wherein the optical scanner is a barcode scanner.

10. A method of tracking a specimen acquired from a patient, the method comprising:

(a) storing in a computer storage of a computer a first machine-readable code present on an identification (ID) means worn by a patient;

(b) storing in the computer storage of the computer a second machine-readable code associated with an order to obtain a specimen from the patient;

(c) storing in the computer storage of the computer a third machine-readable code present on an identification (ID) means worn by a specimen-taker;

(d) selecting from a plurality of specimen containers having machine-readable codes that are unique to each other preapplied thereto one specimen container including a fourth machine-readable code preapplied thereto, wherein the fourth machine-readable code comprises a barcode that encodes a unique serial number and an expiration date of the container;

(e) in response to receiving the fourth machine-readable code from an electronic reading means, a processor of the computer determining from the expiration date encoded in the fourth machine-readable code if the specimen container is out-of-date and, if so, causing an alert signal indicative of said out-of-date condition to be generated by or near the electronic reading means, otherwise, if the specimen container is not out-of-date, and in response to the processor determining that the first machine-readable code and the second machine-readable code are related to the same patient, the processor causing the first—fourth machine-readable codes to be stored in the computer storage in a relational manner and the processor causing a signal to be generated to acquire a specimen from the patient and to place the acquired specimen in the container; and (f) responsive to the processor receiving a signal that the specimen has been placed in the container following step (e), the processor causing an indication thereof to be stored in the computer storage in a relational manner with said first—fourth machine-readable codes, wherein step (f) includes the processor determining whether the signal of step (f) is received within a predetermined time interval of the processor generating the signal of step (e) and storing an indication thereof in the computer storage in a relational manner with said first—fourth machine-readable codes.

11. The method of claim 10, further including:

(g) in response to receiving from the electronic reading means a fifth machine-readable code that is preapplied to another specimen container selected from the plurality of specimen containers, said processor causing the first, second, third, and fifth machine-readable codes to be stored in the computer storage in a relational manner; and (h) responsive to the processor receiving a signal that the other specimen has been placed in the other container following step (g), the processor causing an indication thereof to be stored in the computer storage in a relational manner with said first, second, third, and fifth machine-readable codes.

12. The method of claim 11, wherein each machine-readable code is unique of the other machine-readable codes.

13. The method of claim 10, wherein:

each machine-readable code comprises a unique barcode;
the ID means worn by the patient is a bracelet; and
the ID means worn by the specimen-taker is a badge.

14. The method of claim 10, wherein the first machine-readable code comprises a barcode that encodes at least one of the following: a unique serial number; the patient's name; a registration number assigned to the patient; the patient's date of birth; the patient's sex; a code that signifies the type of ID means worn by the patient; and a check digit.

15. The method of claim 10, wherein the fourth machine-readable code comprises a barcode that encodes at least one of the following: a unique serial number; an expiration date; a color of a lid or cap that specifies the type of specimen the container is to be used for; human readable numbers and/or characters corresponding to one or more of the unique serial number, the expiration date, and the color of the lid; and a check digit.

16. The method of claim 10, wherein the second machine-readable code comprises a barcode that encodes at least one of the following: an order number; a type of specimen to be acquired; a volume of the specimen to be acquired; a time that the specimen is to be acquired; and a control number.

17. The method of claim 10, wherein the electronic reading means is an optical scanner that is communicatively coupled with the computer via a wired or wireless connection.

18. The method of claim 17, wherein the optical scanner is a barcode scanner.

19. A system for tracking one or more specimens acquired from a patient, wherein comprising: a processor of a standalone or networked computer is in operative communication with a computer storage and an electronic reading means that is operative for reading unique machine-readable codes disposed on the following: an identification (ID) means worn by a patient, an order to obtain the one or more specimens from the patient, an identification (ID) means worn by a specimen-taker, and a plurality of specimen containers each for receiving one specimen from the patient, wherein the electronic reading means is also operative for dispatching said machine-readable codes to the processor which, in response to the machine-readable codes for the patient ID means and the order being related to the same patient, stores the machine-readable code for each specimen container to receive a specimen in the computer storage in a relational manner with the machine-readable codes for the patient ID means, the order, and the specimen-taker ID means, and generates a first signal to acquire a specimen from the patient and to place the acquired specimen in the specimen container, wherein the processor is responsive to a second signal that the specimen has been placed in the specimen container within a predetermined time interval of the processor generating the first signal for storing an indication thereof in the computer storage in a relational manner with the machine-readable code for the specimen container that received the specimen stored in the computer storage, wherein each specimen container of the plurality of specimen containers includes a machine-readable code preapplied thereon that is unique from the machine-readable code preapplied to any other of the specimen containers and the machine-readable codes disposed on the patient ID means, the order, and the specimen-taker ID means.

* * * * *

UNITED STATES PATENT AND TRADEMARK OFFICE
CERTIFICATE OF CORRECTION

| | | |
|---|---|---|
| PATENT NO. | : 8,038,055 B2 | Page 1 of 1 |
| APPLICATION NO. | : 12/510546 | |
| DATED | : October 18, 2011 | |
| INVENTOR(S) | : Fredric I. Orkin | |

It is certified that error appears in the above-identified patent and that said Letters Patent is hereby corrected as shown below:

Column 13, Line 10, Claim 19, after "patient" delete "wherein"

Signed and Sealed this
First Day of May, 2012

David J. Kappos
*Director of the United States Patent and Trademark Office*